United States Patent [19]

Gainer

[11] 4,046,880
[45] Sept. 6, 1977

[54] METHOD OF TREATING HYPERTENSION

[75] Inventor: John L. Gainer, Charlottesville, Va.

[73] Assignee: The University of Virginia, Charlottesville, Va.

[21] Appl. No.: 678,551

[22] Filed: Apr. 20, 1976

[51] Int. Cl.² .................... A61K 31/70; A61K 31/20
[52] U.S. Cl. .................................. 424/180; 424/318; 424/319; 424/325; 424/343
[58] Field of Search .............. 424/180, 318, 319, 325, 424/343

[56] References Cited

U.S. PATENT DOCUMENTS 3,853,993  12/1974  Gainer .................................. 424/180

OTHER PUBLICATIONS

*A Testbook of Medicine,* W. B. Saunders Company (1941) pp. 1255-1257.
*Textbook of Organic Medicinal and Pharmaceutical Chemistry,* Wilson et al., 4th Ed., (1962) pp. 607-608.

*Primary Examiner*—Frederick E. Waddell
*Attorney, Agent, or Firm*—Oblon, Fisher, Spivak, McClelland & Maier

[57] ABSTRACT

A method for the treatment of hypertension in mammals comprises administering to said mammal suffering from hypertension an effective dose of a water soluble carotenoid.

6 Claims, 1 Drawing Figure

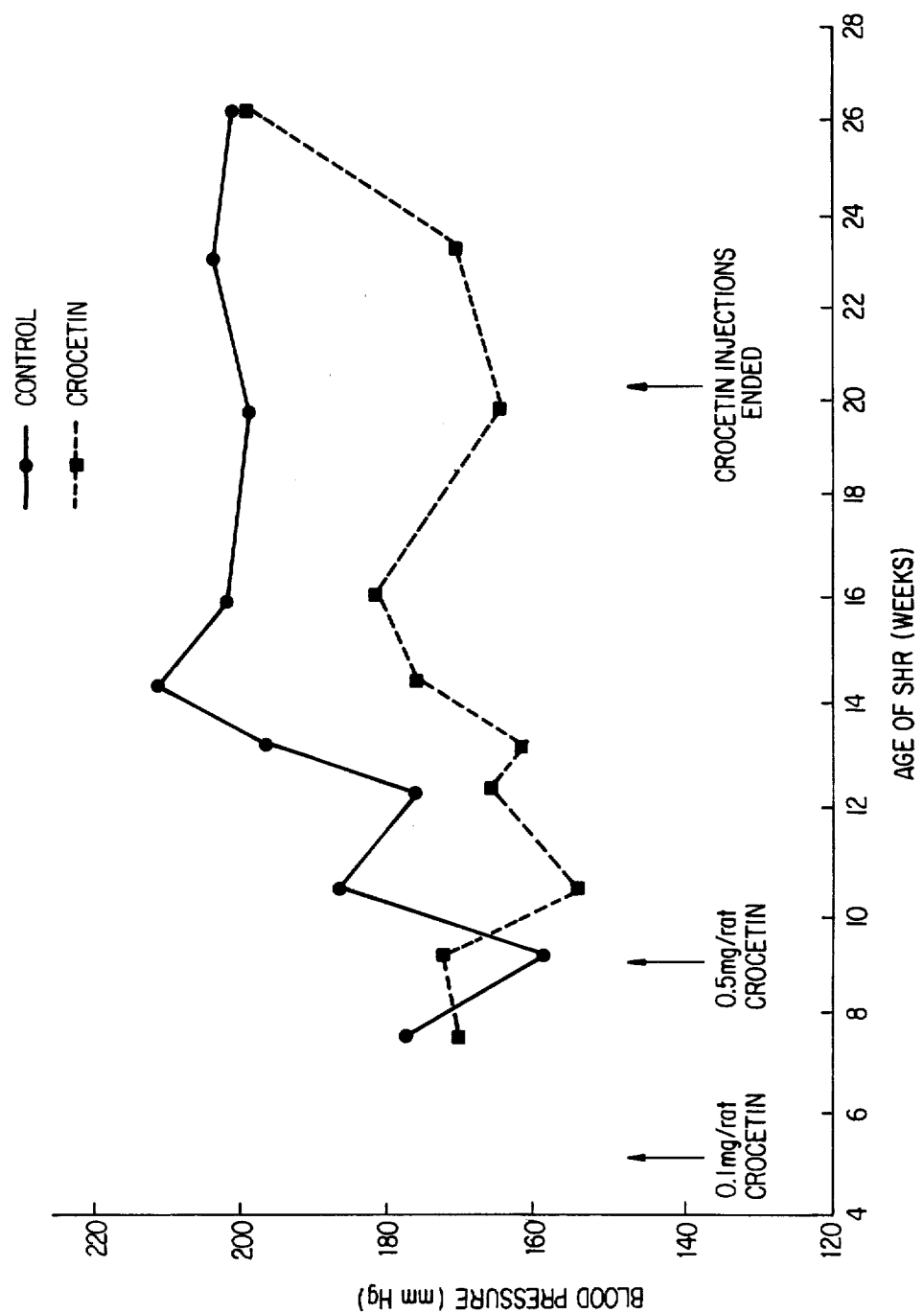

METHOD OF TREATING HYPERTENSION

BACKGROUND OF THE INVENTION

1. Field of the Invention

This invention relates to a novel technique for the treatment of hypertension in mammals.

2. Description of the Prior Art

In applicant's prior applications, now U.S. Pat. Nos. 3,853,993 and 3,788,468; and Ser. No. 572,631, filed Apr. 29, 1975, now U.S. Pat. No. 3,965,261; and Ser. No. 608, 400, filed Aug. 27, 1975; Ser. No. 584,946, filed June 9, 1975, now U.S. Pat. No. 3,975,519; Ser. No. 630,684, filed Nov. 10, 1975; and Ser. No. 634,149 filed Nov. 11, 1975, and Ser. No. 678,113, filed Apr. 19, 1976, now allowed, applicant has disclosed that certain water-soluble carotenoids have been observed to possess quite unique properties.

Applicant has continued the study of these compounds and has now learned of further important properties.

SUMMARY OF THE INVENTION

It has now been found that the water-soluble carotenoid compounds, such as crocetin and crocin, can be used effectively for the treatment of hypertension.

BRIEF DESCRIPTION OF THE DRAWING

A more complete appreciation of the invention and many of the attendant advantages thereof will be readily attained as the same becomes better understood by reference to the following detailed description when considered in connection with the accompanying drawing, wherein:

the FIGURE shows the results of crocetin treatment on the blood pressure in SHR rats.

DETAILED DESCRIPTION OF THE PREFERRED EMBODIMENTS

Hypertension, which is commonly known as high blood pressure, is a very common disease. Another related, very common disease, atherosclerosis, has been successfully treated by applicant using the water-soluble carotenoids used in this application (see U.S. Pat. No. 3,853,993). While there does appear to be a link between the two conditions (for example, it has been reported that hypertension was present in about 70% of deaths due to atherosclerotic heart disease and coronary sclerosis was found in 90% of the hearts of people dying with hypertension — Moriyama, I. M. et al., "Cardiovascular Diseases in the United States", Harvard Press 1971), they are each a unique and separate disease.

For example, atherosclerosis is usually diagnosed through high blood lipid levels (cholesterol and triglycerides) while hypertension is diagnosed by direct measurement of blood pressure. Moreover, the drugs used to treat one disease are in general not used to treat the other.

It has been noted that the lipid contents of various arteries are related to blood pressure [Paterson, J. C. et al., Canad. Med. J., 82, 65 (1960)] and that some antihypertensive drugs produce a parallel fall in serum cholesterol [Baker, A. B. et al., Circulation, 39, 701 (1969)]. However, in pharmaceutical science, the diseases are treated differently, and as two separate conditions since there is no necessary relationship between an antiatherosclerosis drug and an antihypertensive drug. In other words, from the fact that a drug is effective against one disease, nothing can be concluded concerning its likely effectiveness against the other.

The present invention is based on the unexpected discovery that water soluble carotenoids are effective antihypertensives as shown in tests on Spontaneous Hypertensive Rate (SHR), the results of which are given in the Example. The SHR has been shown to be an excellent model of human hypertension [Okamoto, K., "Spontaneous Hypertension — Its Pathogenesis and Complications", Springer-Verlag, New York, 1972], and is, consequently, a standard test animal for testing of antihypertensive drugs.

The carotenoids useful as antihypertensives are those of the form:

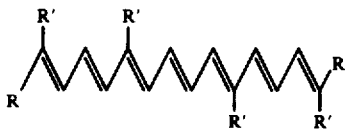

wherein each R may represent a hydrophilic group and each R' represents hydrogen or methyl. Suitable hydrophilic groups include the carboxyl groups or the ester groups of the form COOR" wherein R" represents a soluble sugar group, such as $C_{12}H_{21}O_{10}$, an alkanol group, such as $-CH_2-OH$, $-CH_2-CH_2-OH$, or $-CH_2-CH_2-CH_2-OH$, or a carobxy substituted lower alkyl, such as $-CH_2-COOH$, $-CH_2-CH_2-COOH$ or $-CH_2-CH_2-CH_2COOH$, or each R and R' may represent a lower alkanol group, such as $-CH_2-OH$, $-CH_2-CH_2-OH$, or $-CH_2-CH_2-CH_2-OH$, a hydroxy group, or an amine group of the form $-NH$ or $NR'''$ wherein $R'''$ is a lower alkyl, lower alkanol or carboxy substituted lower alkyl, or a carboxy substituted lower alkyl, such as $-CH_2-CH_2-COOH$, $-CH_2-COOH$, or $-CH_2-CH_2-CH_2-COOH$.

Most preferred are crocetin, also known as 8,8'-diapo-8,8'-carotenoic acid, or crocin, also known as digentiobiosyl 8,8'-diapo-8,8'-carotenedioate, or a salt, such as the sodium salt, of crocetin.

The water soluble carotenoids can be administered to the mammal either orally in the form of a capsule or tablet, or intraveneously or intramuscularly. The effective dosage of the crocetin, of course, will probably depend upon the severity of the condition, the stage and the individual characteristics of each mammal being treated. It is expected, however, that the water-soluble carotenoids, and particularly crocetin or crocin, may be administered in a dosage ranging from about 0.001 mg to 1000 mg of active ingredient per kg of body weight per day, and preferably from 0.005 to 500 mg/kg/day or from 0.001 to 1000 mg per kg of body weight per week.

The carotenoid can be injected into the patient, and in an injectable form, it may be combined with vitamins, choline, glycerophosphoric acid, glycol, glycerine or gum tragacanth or other conventional pharmaceutical additives.

Although the carotenoids have been identified herein as "water soluble carotenoids", it should be understood that they also are soluble in hydrocarbons due to their long chain hydrocarbon structure.

Having generally described the invention, a more complete understanding can be obtained by reference to the following specific example, which is included for purposes of illustration only, and is not intended to be limiting unless otherwise specified.

EXAMPLE

Ten Spontaneous Hypertensive rats were obtained at 1 month of age from Taconic Farms, Germantown, New York. One-half of these were begun on the crocetin treatment, which consisted of an i.p. injection of 0.1 mg of the sodium salt of crocetin in solution for four weeks, followed by daily injections of 0.5 mg of the sodium salt of crocetin, i.p., in each rat. The injections were all performed daily and the blood pressures were measured periodically using the tail-cuff method [McConnell et al., *Proc. Soc. Expt'l. Biol. Med.*, 143, 185 (1973), and Williams, J. D. et al., *J. Clin. Invest.*, 18, 373 (1939)]. The rats were allowed to eat regular lab rat chow and drink water ad libitum.

The results of the blood pressure measurements are shown in the FIGURE. As can be seen, crocetin results in a statistically significant reduction ($p < 0.005$) in the blood pressure at the end of 20 weeks. Further, when crocetin injections were stopped at the end of 20 weeks, the blood pressure returned to the values of the controls, further demonstrating that crocetin reduces blood pressure.

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. A method for the treatment of hypertension in mammals which comprises administering to said mammal suffering from hypertension an antihypertensively effective dose of a water soluble carotenoid.

2. The method of claim 1, wherein said water soluble carotenoid has the formula:

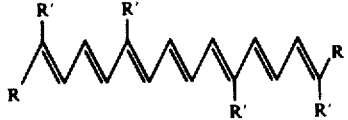

wherein each R is a hydrophilic group, and wherein each R' is hydrogen or methyl.

3. The method of claim 1, wherein said water-soluble carotenoid is crocin.

4. The method of claim 1, wherein said water-soluble carotenoid is crocetin, or a salt thereof.

5. The method of claim 4, wherein said water-soluble carotenoid is the sodium salt of crocetin.

6. The method of claim 1, wherein said water-soluble carotenoid is administered intraveneously or intraperitoneally at a dose rate of from 0.001 mg to 1000 mg active ingredient per kg of body weight per week.

* * * * *